United States Patent [19]

Weber et al.

[11] Patent Number: 5,082,839
[45] Date of Patent: Jan. 21, 1992

[54] THIENO-TRIAZOLO-1,4-DIAZEPINO-2-CARBOXYLIC ACID AMIDES

[75] Inventors: Karl-Heinz Weber, Gau-Algesheim; Albrecht Harreus, Ludwigshafen; Jorge Casals-Stenzel, Munich; Gojko Muacevic, Ingelheim am Rhein; Wolfgang Tröger, Stromberg; Gerhard Walther, Bingen am Rhein, all of Fed. Rep. of Germany

[73] Assignee: Boehringer Ingelheim GmbH, Ingelheim am Rhein, Fed. Rep. of Germany

[21] Appl. No.: 539,416

[22] Filed: Jun. 15, 1990

Related U.S. Application Data

[60] Division of Ser. No. 252,725, Oct. 3, 1988, Pat. No. 4,968,794, which is a continuation-in-part of Ser. No. 821,640, Jan. 23, 1986, abandoned.

[30] Foreign Application Priority Data

Jan. 25, 1985 [DE] Fed. Rep. of Germany ....... 3502392

[51] Int. Cl.$^5$ .................... A61K 31/33; A61K 31/41; A61K 31/55; C07D 487/04
[52] U.S. Cl. .................................... 514/220; 540/496; 540/497; 540/498; 540/499
[58] Field of Search ............... 540/496, 497, 498, 499; 514/220

[56] References Cited

U.S. PATENT DOCUMENTS

| | | | |
|---|---|---|---|
| 4,201,712 | 5/1980 | Weber et al. | 540/560 |
| 4,621,083 | 11/1986 | Casals-Stenzel et al. | 514/220 |
| 4,900,729 | 2/1990 | Stransky et al. | 514/220 |
| 4,914,096 | 4/1990 | Houlikan et al. | 514/220 |
| 4,959,361 | 9/1990 | Walser | 514/220 |
| 4,960,770 | 10/1990 | Moriwaki et al. | 514/220 |
| 4,968,794 | 11/1990 | Weber et al. | 540/560 |

FOREIGN PATENT DOCUMENTS 2503235  7/1976  Fed. Rep. of Germany.

OTHER PUBLICATIONS

Kornecki et al., Science vol. 226, p. 1454 (1984).

Stransky et al., Chem. Abst. 107-198366t (1987).

*Primary Examiner*—Cecilia Shen
*Attorney, Agent, or Firm*—D. E. Frankhouser; M-E. M. Timbers; A. R. Stempel

[57] ABSTRACT

The invention relates to new thieno-triazolo-1,4-diazepino-2-carboxylic acid amides of formula I

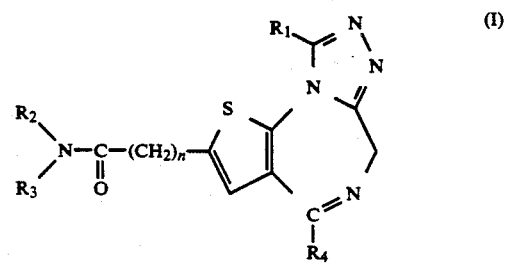

wherein
$R_1$ represents hydrogen, a $C_1$-$C_4$ straight-chained or branched alkyl which can optionally be substituted by halogen, preferably Cl or Br, or by hydroxy, cyclopropyl, $C_1$-$C_3$ alkoxy, preferably methoxy, or halogen, preferably chlorine or bromine;
$R_2$ and $R_3$, each independently, represent hydrogen, a $C_1$-$C_4$ straight-chained or branched alkyl, $C_1$-$C_4$ hydroxyalkyl or the two groups $R_2$ and $R_3$ together with the nitrogen atom represent a 5-, 6- or 7-membered ring which optionally contains a nitrogen, oxygen or sulfur atom as a further heteroatom, the second nitrogen atom optionally being substituted by a $C_1$-$C_4$ alkyl, preferably a methyl group;
$R_4$ represents alpha-pyridyl or a phenyl in which the phenyl ring can be substituted preferably in the 2-position, by methyl, halogen, preferably chlorine or bromine, nitro or trifluoromethyl;
n represents one of the numbers 0, 1, 2, 3, 4, 5, 6, 7 or 8; and novel intermediates therefor.

The compounds of formula I are useful in the treatment of pathological conditions and diseases in which platelet activating factor is implicated.

7 Claims, 1 Drawing Sheet

Fig. 1

THIENO-TRIAZOLO-1,4-DIAZEPINO-2-CARBOXYLIC ACID AMIDES

This is a division of application Ser. No. 252,725, filed Oct. 3, 1988. Now U.S. Pat. No. 4,968,794 which is a continuation-in-part of prior U.S. Ser. No. 821,640, filed Jan. 23, 1986, now abandoned.

The invention relates to new thieno-triazolo-1,4-diazepino-2-carboxylic acid amides of formula I:

wherein:

$R_1$ represents hydrogen, a $C_1$–$C_4$ straight-chained or branched alkyl which can optionally be substituted by halogen, preferably Cl or Br, or by hydroxy, cyclopropyl, $C_1$–$C_3$ alkoxy, preferably methoxy, or halogen, preferably chlorine or bromine;

$R_2$ and $R_3$, each independently, represent hydrogen, a $C_1$–$C_4$ straight-chained or branched alkyl, $C_1$–$C_4$ hydroxyalkyl or the two groups $R_2$ and $R_3$ together with the nitrogen atom represent a 5-, 6- or 7-membered ring which optionally contains a nitrogen, oxygen or sulfur atom as a further heteroatom, the second nitrogen atom optionally being substituted by a $C_1$–$C_4$ alkyl, preferably a methyl group;

$R_4$ represents alpha-pyridyl or a phenyl in which the phenyl ring can be substituted, preferably in the 2-position, by methyl, halogen, preferably chlorine or bromine, nitro or trifluoromethyl;

n represents one of the numbers 0, 1, 2, 3, 4, 5, 6, 7 or 8.

Unless otherwise stated, halogen represents one of the halogen atoms fluorine, chlorine, bromine or iodine.

One subgeneric aspect includes compounds of formula I wherein n represents one of the numbers 0, 1 or 2, and particularly those wherein n=2.

Another subgeneric aspect includes alkyl groups selected from methyl, ethyl, propyl, isopropyl, butyl and tert.butyl groups.

The compounds of formula I can be obtained in conventional manner from the corresponding 2-carboxylic acids of formula II:

wherein $R_1$ and $R_4$ are as defined, above a) by reaction with the desired amine in the presence of a carbodiimide or carbonyldiimidazole, or b) by converting the free acid into an acid halide or acid anhydride and subsequently reacting with the desired amine.

The reaction of the free acid with the amine is carried out in the presence of a carbodiimide, for example cyclohexylcarbodiimide or carbonyldiimidazole in an inert solvent such as dimethylformamide, tetrahydrofuran, dioxan, etc., at temperatures of between 0° C. and the boiling point of the reaction mixture.

When the amine is reacted with an acid halide or acid anhydride, the amine is reacted with the acid halide or acid anhydride in an inert solvent, for example dimethylformamide, tetrahydrofuran, dioxan or a suitable hydrocarbon such as benzene or toluene at temperatures of between ambient temperature and the boiling point of the reaction mixture, optionally with the addition of an acid binding agent such as sodium carbonate, sodium bicarbonate or a tertiary organic base, e.g. pyridine or triethylamine.

If the amine is a liquid, the reaction may also be carried out in an excess of the amine without any added solvent.

The acid halide or anhydride is obtained from the free acid in conventional manner, e.g. by reacting the acid with a thionyl halide or by reacting an alkali metal salt of the acid with acetyl chloride or chloroformic acid chloride.

Using the processes described above, the following end products can be obtained, for example:

a) 2-[4-(2-Chlorophenyl)-9-methyl-6H-thieno[3,2-f][1,2,4]-triazolo[4,3-a][1,4]diazepin-2-yl]-ethane-1-carboxylic acid morpholide;

b) 2-[4-(2-Chlorophenyl)-9-cyclopropyl-6H-thieno[3,2-f]-[1,2,4]triazolo[4,3-a][1,4]diazepin-2-yl]-ethane-1-carboxylic acid morpholide;

c) [4-(2-Chlorophenyl)-9-methyl-6H-thieno[3,2-f][1,2,4]-triazolo[4,3-a][1,4]diazepin-2-yl]-carboxylic acid morpholide;

d) [4-(2-Chlorophenyl)-9-methyl-6H-thieno[3,2-f][1,2,4]-triazolo[4,3-a][1,4]diazepin-2-yl]-carboxylic acid amide:

e) 2-[4-(2-Chlorophenyl)-9-methyl-6H-thieno[3,2-f][1,2,4]-triazolo[4,3-a][1,4]diazepin-2-yl]-ethane-1-carboxylic acid diethylamide;

f) 8-[4-(2-Chlorophenyl)-9-cyclopropyl-6H-thieno[3,2-f]-[1,2,4]triazolo[4,3-a][1,4]diazepin-2-yl]-n-octane-1-carboxylic acid morpholide;

g) 2-[4-(2-Chlorophenyl)-9-methyl-6H-thieno[3,2-f][1,2,4]-triazolo[4,3-a][1,4]diazepin-2-yl]-ethane-1-carboxylic acid N,N-di-(2-hydroxyethyl)amide];

h) 2-[4-(2-Chlorophenyl)-9-methyl-6H-thieno[3,2-f][1,2,4]-triazolo[4,3-a][1,4]diazepin-2-yl]-ethane-1-carboxylic acid methylamide;

i) 2-[4-(2-Chlorophenyl)-9-methyl-6H-thieno[3,2-f][1,2,4]-triazolo[4,3-a][1,4]diazepin-2-yl]-ethane-1-carboxylic acid isopropylamide;

j) 2-[4-(2-Chlorophenyl)-9-methyl-6H-thieno[3,2-f][1,2,4]-triazolo[4,3-a][1,4]diazepin-2-yl]-ethane-1-carboxylic acid dimethylamide;

k) 2-[4-(2-Chlorophenyl)-9-methyl-6H-thieno[3,2-f][1,2,4]-triazolo[4,3-a][1,4]diazepin-2-yl]-ethane-1-carboxylic acid N'-methyl-piperazide;

l) 2-[4-(2-Chlorophenyl)-9-methyl-6H-thieno[3,2-f][1,2,4]-triazolo[4,3-a][1,4]diazepin-2-yl]-ethane-1-carboxylic acid pyrrolidide;

m) 2-[4-(2-Chlorophenyl)-9-methyl-6H-thieno[3,2-f][1,2,4]-triazolo[4,3-a][1,4]diazepin-2-yl]-ethane-1-carboxylic acid piperidide;

n) 2-[4-(2-Chlorophenyl)-9-cyclopropyl-6H-thieno[3,2-f]-[1,2,4]triazolo[4,3-a][1,4]diazepin-2-yl]-ethane-1-carboxylic acid diethylamide;

o) 2-[4-(2-Chlorophenyl)-6H-thieno[3,2-f][1,2,4]triazolo-[4,3-a][1,4]diazepin-2-yl]-ethane-1-carboxylic acid morpholide;

p) 2-[4-(2-Chlorophenyl)-9-bromo-6H-thieno[3,2-f][1,2,4]-triazolo[4,3-a][1,4]diazepin-2-yl]-ethane-1-carboxylic acid morpholide;

q) 2-[4-(2-Chlorophenyl)-9-methoxy-6H-thieno[3,2-f][1,2,4]-triazolo[4,3-a][1,4]diazepin-2-yl]-ethane-1-carboxylic acid morpholide;

r) 2-[4-Phenyl-9-methyl-6H-thieno[3,2-f][1,2,4]triazolo-[4,3-a][1,4]diazepin-2-yl]-ethane-1-carboxylic acid morpholide;

s) 2-[4-(2-Nitrophenyl)-9-methyl-6H-thieno-[3,2-f][1,2,4]-triazolo[4,3-a][1,4]diazepin-2-yl]-ethane-1-carboxylic acid morpholide;

t) 2-[4-(2-Methylphenyl)-9-methyl-6H-thieno-[3,2-f][1,2,4]-triazolo[4,3-a][1,4]diazepin-2-yl]-ethane-1-carboxylic acid morpholide;

u) 2-[4-(2-Trifluoromethylphenyl)-9-methyl-6H-thieno-[3,2-f][1,2,4]triazolo[4,3-a][1,4]diazepin-2-yl]-ethane-1-carboxylic acid morpholide;

v) 2-[4-(2-Chlorophenyl)-9-methoxy-6H-thieno[3,2-f][1,2,4]-triazolo[4,3-a][1,4]diazepin-2-yl]-ethane-1-carboxylic acid diethylamide;

w) 2-[4-(2-Chlorophenyl)-9-methoxy-6H-thieno[3,2-f][1,2,4]-triazolo[4,3-a][1,4]diazepin-2-yl]-ethane-1-carboxylic acid piperidide; and x) 2-[4-(2-Chlorophenyl)-9-methoxy-6H-thieno[3,2-f][1,2,4]-triazolo[4,3-a][1,4]diazepin-2-yl]-ethane-1-carboxylic acid N'-methylpiperazide.

The starting materials of formula II are for the most part new compounds. They are obtained, starting from the corresponding aldehydes, according to the reaction scheme shown in FIG. 1, in which R represents a methyl or ethyl alkylcarboxylate or methyl or ethyl alkyldicarboxylate.

Figure 1:
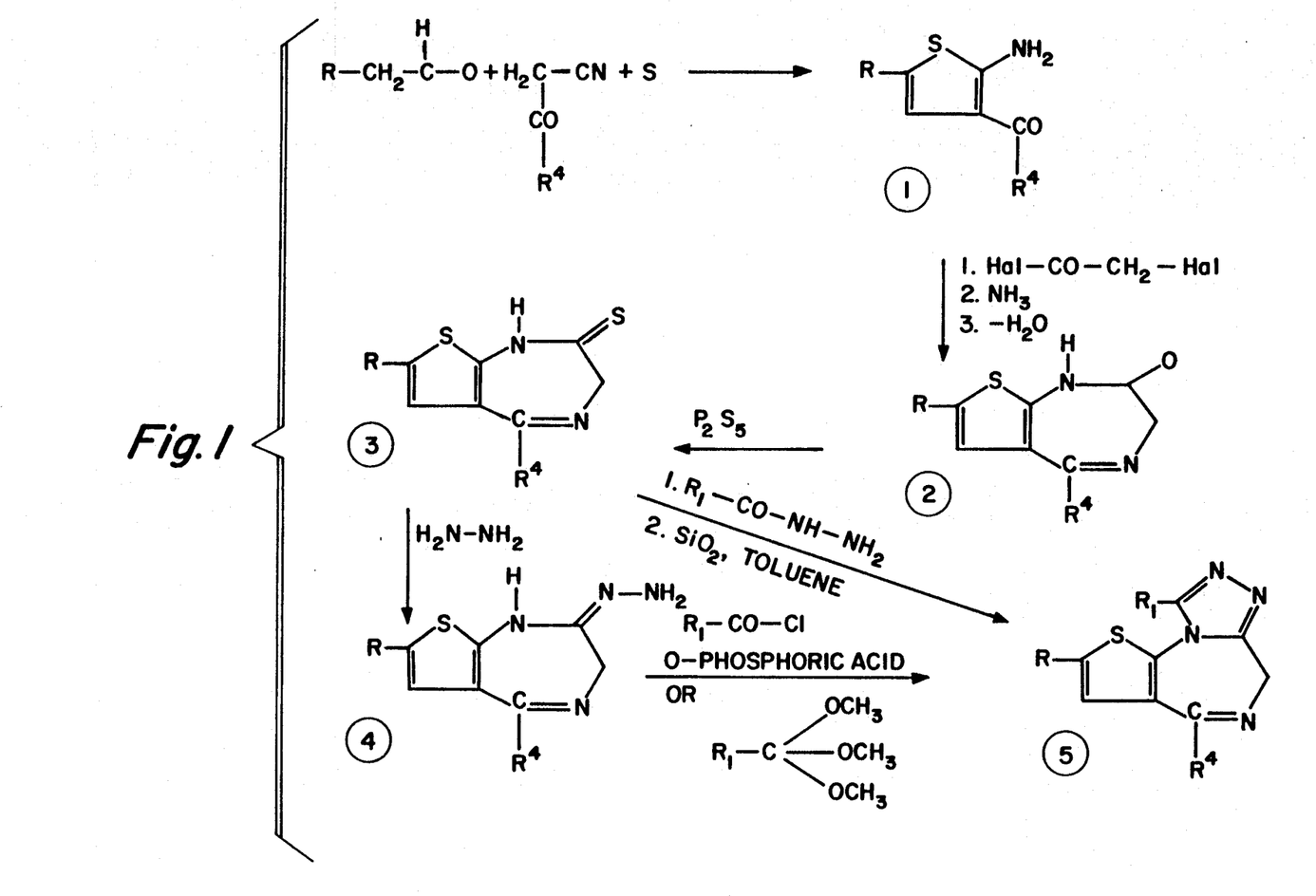

If a dicarboxylic acid ester is used, one of the carboxyl groups is split off at the stage of the aminoketone after saponification.

To obtain $R_1$=hydrogen, either one uses as starting material a compound of formula (3) which is reacted with formic acid hydrazide to produce a compound of formula (5) or a compound of formula (4) is reacted with an o-formic acid ester.

To obtain $R_1$=chlorine or bromine, first of all a compound wherein $R_1$=hydrogen is prepared and then this is reacted with chlorine or bromine in pyridine.

The 1-methoxy compound is obtained from a chlorine or bromine compound as mentioned above by reacting with sodium methoxide.

Compounds wherein n represents 0 are obtained from compounds with a carboxyl group in the 1 position as described in DOS 2503235; the free acid is reacted further as mentioned above.

The compounds according to the invention have a PAF-antagonistic activity.

As is known, PAF (platelet activating factor) is the phospholipid acetyl-glyceryl-ether-phosphoryl-choline (AGEPC) which is known as a potent lipid mediator released by animal and human proinflammatory cells. These cells include mainly basophilic and neutrophilic granulocytes, macrophages (from blood and tissue) and thrombocytes which are involved in inflammatory reactions.

PAF exhibits bronchoconstriction, a lowering of blood pressure, the triggering of thrombocyte aggregation and a proinflammatory activity.

PAF antagonists are useful to treat pathological conditions and diseases in which PAF is implicated. Examples of indications of a PAF antagonist are inflammatory processes of the tracheobronchial tree (acute and chronic bronchitis, bronchial asthma) or of the kidneys (glomerulonephritis), anaphylactic conditions, allergies and inflammation in the mucous membranes and skin (e.g. psoriasis) and states of shock induced by sepsis, endotoxins or burns.

Further important indications for a PAF-antagonistic are lesions and inflammation in the stomach- and intestinal mucosal membrane, for example gastritis, in general peptic ulcus, but especially ventricular ulcus and duodenal ulcus.

The PAF-antagonistic effect of individual benzodiazepines is known, cf., E. Kornecki et al., Science 226, 1454–1456 (1984). These compounds which are commercially available and have proved themselves as tranquilizers and hypnotics are, however, unsuitable for use as PAF antagonists in therapy in many instances because of their marked CNS activity.

The compounds according to the invention, on the other hand, lack any CNS activity, while the PAF-antagonistic activity is up to fifty times greater than that of the known benzodiazepines.

For example, the following compounds were tested in the benzodiazepine receptor bonding test using [3H] flunitrazepam as radioligand (Bechtel et al. in Arneimittelforschung 3a, 1986, 534).

TABLE A

| Example No. | 3H flunitracepam receptor bonding test $10^{-9}$ Mol |
| --- | --- |
| 1 | 400 |
| 4 | 56 |
| 5 | 415 |
| 12 | 43 |
| 15 | 295 |
| 16 | 625 |
| Etizolam | 5 |
| Brotizolam | 1 |
| Triazolam | 9 |

The following Examples serve to illustrate the invention:

EXAMPLE 1

2-[4-(2-Chlorophenyl)-9-methyl-6H-thieno[3,2-f][1,2,4]-triazolo[4,3-a][1,4]diazepin-2-yl]-ethane-1-carboxylic acid morpholide First, 2-[4-(2-chlorophenyl)-9-methyl-6H-thieno-[3,2-f][1,2,4]-triazolo[4,3-a][1,4]diazepin-2-yl]-ethane-1-carboxylic acid (5.3 g, 0.014 mol), N-hydroxybenzotriazole (HOBT) (1.8 g) and absolute dimethylformamide (60 ml) are mixed with morpholine (1.2 g, 0.014 mol) with stirring at ambient temperature, to form a clear solution. Then, at 0° to 5° C., over a period of 5 to 10 minutes, dicyclohexylcarbodiimide (3.5 g) in solid form is added and the temperature is maintained at 0° to 10° C. for a further 6 to 8 hours. The dicyclohexylurea precipitated is suction filtered, washed with a little cold dimethylformamide and the filtrate is concentrated by evaporation in vacuo. The residue is dissolved in methylene chloride, washed with 5% soda solution and ice water. The organic phase is evaporated and the residue is crystallized using ethyl acetate. Yield: 5.2 g colorless crystals, m.p. 189°-190° C.

$^1$NMR (CDCl$_3$), $\delta$=2.64 (2t, —CH$_2$—CO—), 2.71 (3s, CH$_3$), 3.17 (2t, CH$_2$), 3.33-3.81 (8m, morpholine), 4.96 (2s, CH$_2$), 6.48 (1s, thiophene), 7.28-7.60 (4m, aryl).

The starting material is obtained as follows: it is new:

a)
2-Amino-3-o-chlorobenzoyl-5-(2-dicarbethoxyethyl)-thiopene

Here, o-chlorocyanoacetophenone (53.9 g, 0.3 mol), sulfur (9.6 g) and dimethylformamide (120 ml) are mixed with dicarbethoxybutyraldehyde (64.8 g, 0.3 mol) (D. T. Warner, J. Am. Chem. Soc. 70, 3470 (1948); Bp. 97° C./0.1 mbar) with stirring, initially at ambient temperature, but with the temperature rising to 45°-50° C. The mixture is stirred for 2 to 3 hours at 60° to 70° C., cooled to ambient temperature and water (400 ml) is added. The thiophene derivative formed is extracted three times with methyl-tert.butyl-ketone (200 ml). After washing with water and drying of the organic phase it is evaporated and the crystalline residue is recrystallized from isopropanol/water 7:3. Yield 90 g, m.p. 96°-98° C.

b)
2-Amino-o-chlorobenzoyl-5-(2-carbomethoxyethyl)-thiophene

The above compound (63 g, 0.15 mol) is refluxed for 2 hours with ethanol (120 ml) and caustic potash (32.5 g) in water (50 ml). The mixture is concentrated in vacuo, diluted with water (50 ml) and acidified with HCl. The greasy acid precipitate is extracted several times with ethyl acetate. The extracts are dried and concentrated by evaporation and the residue is refluxed for 2 hours with toluene (300 ml) and dimethylformamide (30 ml). After evaporation (to about 50 ml), crystals of the monocarboxylic acid are obtained.

Yield: 20.5 g. The purified acid melts at 171°-173° C.

The crude acid is stirred for 18 hours at ambient temperature together with absolute methanol (400 ml) and concentrated sulfuric acid (0.4 ml). After evaporation of the methanol the residue is poured onto ice, extracted with methylene chloride and, after re-evaporation from isopropylether, the ester (15 g) is obtained, m.p. 89°-90° C.

c)
2-Bromoacetylamino-3-o-chlorobenzoyl-5-(2-carbomethoxyethyl)-thiophene

The above ester (27.8 g, 0.09 mol) is suspended in toluene (700 ml) and mixed with sodium bicarbonate (10 g) in water (57 ml). Bromoacetylbromide (7.9 ml) is gradually added at 40° to 50° C. with stirring and the mixture is stirred for a further 30 minutes. It is washed with water, the toluene is dried, evaporated in vacuo and brought to crystallization with isopropylether.

Yield: 35-37 g, m.p. 104°-160° C.

d)
2-Aminoacetylamino-3-o-chlorobenzoyl-5-(2-carbomethoxyethyl)-thiophene

The above bromoacetyl compound (35.8 g, 0.08 mol) is dissolved in ethyl acetate (700 ml) and dry ammonia is introduced at ambient temperature with stirring over a period of 2 to 3 hours. The mixture is left to stand overnight, washed with iced water, dried, evaporated and an oily amino compound (22-25 g) is obtained.

e)
7-(2-Carbomethoxyethyl)-5-o-chlorophenyl-thieno-1,4-diazepinone

The above compound (21.3 g, 0.056 mol) is dissolved in toluene (500 ml) and refluxed for 2 hours with silica gel (75 g) using a water separator. The SiO$_2$ is removed by suction filtering and the diazepine is extracted with hot methanol. After evaporation of the methanol, diazepine (12-15 g) is obtained, m.p. 160°-162° C.

f)
7-(2-Carbomethoxyethyl)-5-o-chlorophenyl-thieno-1,4-diazepin-2-thione

The above diazepinone (10 g, 0.03 mol) is stirred in diglyme (100 ml) with phosphorus pentasulfide (6.8 g) and sodium hydrogen carbonate (5 g) for 3 hours at 70°-80° C. The suspension is poured onto ice, stirred for 30 to 45 minutes and the crystals are suction filtered. After drying, thione (10 g) is obtained, m.p. 185°-186° C.

g) Methyl 2-[4-(2-chlorophenyl)-9-methyl-6H-thieno[3,2-f][1,2,4]triazolo[4,3-a][1,4]diazepin-2-yl]ethane-1-carboxylate The above sulfur compound (6.1 g, 0.016 mol) is dissolved in tetrahydrofuran (100 ml) and, after the addition of hydrazine hydrate (1 g), stirred for 30 minutes at 45°-50° C. Then the mixture is evaporated in vacuo. The oil which remains (5 to 5.2 g), crystallizes with isopropylether (m.p. 175°-177° C.).

On being heated in ortho-acetic acid ester (35 ml) to 80° C. and evaporation from methylene chloride/ether, the hydrazino compound yields the triazolodiazepine (3 g), m.p. 114°-115° C.

The same compound can be obtained from the thione with acetic acid hydrazide.

After saponification in alcoholic-aqueous potassium hydroxide solution, the methylester (6.1 g) yields the free carboxylic acid (5.7-5.8 g), m.p. 196°-198° C.

EXAMPLE 2

2-[4-(2-Chlorophenyl)-9-cyclopropyl-6H-thieno[3,2-f][1,2,4]triazolo[4,3-a][1,4]diazepin-2-yl]-ethane-1-carboxylic acid morpholide Starting from 2-[4-(2-chlorophenyl)-9-cyclopropyl-6H-thieno[3,2-f][1,2,4]triazolo[4,3-a]-[1,4]diazepin-2-yl]-ethane-1-carboxylic acid (15 g), m.p. 227°-230° C. the title compound is obtained with the aid of dicyclohexylcarbodiimide and morpholine using the method described in Example 1. Yield: 15.0 g, m.p. 159°-160° C.

$^1$H-NMR (CDCl$_3$); $\delta$=0.96-1.40 (4m, cyclopropyl —CH$_2$—), 1.93-2.28 (1m, cyclopropyl) 2.64 (2t, CH$_2$—CO—), 3.15 (2t, CH$_2$), 3.31-3.77 (8m, morpholine), 4.91 (2s, CH$_2$-7-ring) 6.44 (1s, thiophene), 7.22-7.60 (4m, aryl)

The starting compound is obtained as follows. First, 7-(2-carbomethoxyethyl)-5-o-chlorophenyl-thieno-1,4-diazepin-2-thione (cf. Example 1) (38 g, 0.1 mol), m.p. 185°-186° C., is refluxed for 1 hour with cyclopropylcarboxylic acid hydrazide (11 g) in dioxan (50 ml) for 1 hour. After evaporation, on trituration with ether, red crystals (30 g) remain, m.p. 148°-150° C., which are heated in toluene (1 liter) in the presence of silica gel (140 g) for 4 hours using a water separator. The mixture is then cooled, suction filtered and the triazolo compound is extracted with hot methanol. A viscous oil (24 g) remains as the residue from the extraction and this oil is saponified by boiling for 1 hour in 2N alcoholic potassium hydroxide solution (250 ml). After working up in the usual way, the carboxylic acid (15-18 g) is obtained, which can be converted directly into the amide.

EXAMPLE 3

[4-(2-Chlorophenyl)-9-methyl-6H-thieno[3,2-f][1,2,4]triazolo[4,3-a][1,4]diazepin-2-yl]-carboxylic acid morpholide The corresponding carboxylic acid (36 g. 0.1 mol) (K. H. Weber et al. DOS 2503235, 7/29/76, p. 14) with a melting point of 302° C. is reacted with morpholine (10 g) in the presence of dicyclohexylcarbodiimide in dimethylformamide as described in Example 1. A viscous oil (38 g) is obtained.

$^1$H-NMR (CDCl$_3$); $\delta$=2.75 (3s, CH$_3$), 3.71 (8s, morpholine), 4.97 (2s CH$_2$-7-ring) 6.83 (1s, thiophene) 7.26-7.64 (4m, aryl)

Starting from 2-amino-3-(2-chlorobenzoyl)-thiophene-5-carboxylic acid (O. Hromatka, Monatsh. Chem. 164, 973 (1973)) the morpholide, m.p. 206°-208° C., is obtained via the corresponding acid chloride. This morpholide can also be converted into the title compound in the manner described in Example 1.

EXAMPLE 4

[4-(2-Chlorophenyl)-9-methyl-6H-thieno[3,2-f][1,2,4]triazolo[4,3-a][1,4]diazepin-2-yl]-carboxylic acid amide The corresponding methyl carboxylate (3.7 g, 0.01 mol) (K. H. Weber et al, DOS 2503235, 7/29/1976, p. 14), m.p. 230°-232° C., is dissolved in methanol (100 ml) and ammonia is introduced with stirring at ambient temperature until saturation is reached. The mixture is then stirred for a further 2 days at 20°-25° C., the solvent is evaporated off and chromatographed over SiO$_2$ (elution with methylene chloride/methanol 9:1)

Yield: 3.5 g, m.p. 300° C. (decomp).

$^1$H-NMR (CDCl$_3$); $\delta$=2.66 (3s, CH$_3$), 4.85 (2s, CH$_2$), 7.50 (1s, thiophene), 7.52 (4H, aryl), 7.65 and 8.25 (2s, NH$_2$)

EXAMPLE 5

2-[4-(2-Chlorophenyl)-9-methyl-6H-thieno[3,2-f][1,2,4]-triazolo[4,3-a][1,4]diazepin-2-yl]-ethane-1-carboxylic acid diethylamide The corresponding carboxylic acid (3.87 g, 0.01 mol) (see Example 1) is stirred in methylene chloride (50 ml) with pure thionylchloride (1 ml) for 2 hours at 30°-35° C. Then diethylamine (8 ml) is added whilst cooling with ice and the mixture is stirred for a further 30 minutes. The salts are washed out with water, the methylene chloride phase is dried, partly evaporated and chromatographed over SiO$_2$ for final purification (eluant: methylene chloride containing 4% added methanol). A viscous oil (1.8-2.0 g) is obtained.

$^1$H-NMR (CDCl$_3$); $\delta$=1.09 and 1.12 (2×3 t, C$_2$H$_5$) 2.52 (2t CH$_2$-CO), 2.72 (3s, CH$_3$), 3.03-3.56 (6m, C$_2$H$_5$ and CH$_2$), 4.90 (2s, CH$_2$-7-ring), 6.44 (1s, thiophene), 7.25-7.55 (4m aryl)

EXAMPLE 6

[4-(2-Chlorophenyl)-9-methyl-6H-thieno[3,2-f][1,2,4]triazolo[4,3-a][1,4]-diazepin-2-yl]-methane carboxylic acid morpholide Here, [4-(2-chlorophenyl)-9-methyl-6H-thieno[3,2-f][1,2,4]-triazolo[4,3-a][1,4]diazepin-2-yl]-methane carboxylic acid (20 g, 0.054 mol), tetrahydrofuran (500 ml) and 1,1'-carbonyldiimidazole (10 g) are stirred for 1 hour at ambient temperature and the solution, now clear, is mixed with morpholine (0.06 mol, 5.2 g). After stirring overnight at ambient temperature, evaporation, taking up in methylene chloride, washing with sodium bicarbonate solution and filtering through a column of SiO$_2$, the title compound (9.4 g), m.p. 143°-144° C., is obtained by recrystallization from ethyl acetate.

$^1$H-NMR (CDCl$_3$): $\delta$=2.74 (3s, CH$_3$), 3.36-3.82 (8 m, morpholine), 3.88 (2s, CH$_2$—CO), 4.97 (2s, CH$_2$-7-ring), 6.51 (1s, thiophene), 7.25-7.60 (4m, aryl).

The carboxylic acid is obtained as follows. Diethyl malonate and bromoacetaldehyde acetal yield the dicarbethoxypropionaldehyde (Bp$_{0.01}$: 92°-95° C.) by methods known from the literature, and this latter is converted analogously to Example 1 with chlorocyanoacetophenone and sulfur into the corresponding 2-aminobenzoylthiophene. Saponification, decarboxylation and esterification with methanol/sulphuric acid yield the 2-amino-3-(o-chlorobenzoyl)-5-(carbomethoxymethyl)-thiopene, bromoacetylation, amination and cyclizing yield the corresponding diazepinone of m.p. 180°-182° C. The thione obtained from this melts at 184°-185° C. Treatment of the thione with hydrazine and subsequent reaction with orthoacetic acid ester yields the methyl triazolothienocarboxylate, m.p. 139°-141° C.; subsequent saponification with alcoholic-aqueous potassium hydroxide solution yields the free carboxylic acid, m.p. 257°-259° C.

EXAMPLE 7

3-[4-(2-Chlorophenyl)-9-methyl-6H-thieno[3,2-f][1,2,4]-triazolo-[4,3-a][1,4]-diazepin-2-yl]-propane-1-carboxylic acid morpholide Analogously to Example 6, 3-[4-(2-chlorophenyl)-9-methyl-6H-thieno[3,2-f][1,2,4]triazolo[4,3-a][1,4]-diazepin-2-yl]-propane-1-carboxylic acid (10 g, 0.025 mol) is reacted in tetrahydrofuran with morpholine and 1,1'-carbonyldiimidazole and, after chromatographic working up, yields a viscous, almost colorless oil (10.5 g).

$^1$H-NMR (CDCl$_3$): $\delta$2.00 (2m, CH$_2$), 2.37 (2m, CH$_2$CO), 2.71 (3s, CH$_3$), 2.87 (2m, CH$_2$), 3.26-3.83 (8m, morpholine), 4.94 (2s, CH$_2$-7-ring), 6.41 (1s, thiophene), 7.24-7.61 (4m, aryl).

The starting material is obtained as follows. Starting from cyclohexanone and using methods known from the literature (L. Claisen, Ber.dtsch. chem. Ges. 40, (3907)), the enolether is obtained which is then subjected to ozonolysis (V. Schmid, P. Grafen, Liebigs Ann. Chem. 656, 97 (1962)). Methyl 5-formylvalerate is obtained, which is reacted as already described to form the 2-amino-benzoyl-thiophene-2-propane carboxylic acid ester. The thiophenediazepinone obtained from this melts at 152°-153° C. Further reaction with phosphoruspentasulphide analogously to Example 1 f) yields the thione, m.p. 176°-178° C. Reaction with hydrazine and with orthoacetic acid ester according to Example 1 g) result in the corresponding ester, which is saponified with alcoholic potassium hydroxide solution to yield the carboxylic acid (melting point: 257°–259° C.).

EXAMPLE 8

4-[4-(2-Chlorophenyl-9-methyl-6H-thieno[3,2-f][1,2,4]-traizolo[4,3-a][1,4]-diazepin-2-yl]-butane-1-carboxylic acid morpholide Here, 4-[4-(2-chlorophenyl)-9-methyl-6H-thieno[3,2-f]-[1,2,4]triazolo-[4,3-a][1,4]-diazepin-2-yl]-butane-1-carboxylic acid (15 g, 0.036 mol) yields the title compound as a bright yellow viscous oil (yield 13 g) when reacted analogously to Example 1 with morpholine and dicyclohexyl-carbodiimide in dimethylformamide as the solvent.

$^1$H-NMR (CDCl$_3$); δ1.72 (4m, —CH$_2$-CH$_2$—), 2.87 (2m, CH$_2$CO), 2.71 (3s, CH$_3$), 2.83 (2m, CH$_2$), 3.30–3.77 (8m, morpholine), 4.93 (2s, CH$_2$-7-ring), 6.41 (1s, thiophene), 7.21–7.58 (4m, aryl).

The carboxylic acid is obtained starting from commercial cycloheptanone analogously to Example 7 via the corresponding aldehyde, bp$_{15}$: 115°–120° C., the methyl thienotriazolo-1,4-diazepin-2-butanecarboxylate, m.p. 119°–121° C., is obtained after saponification of the latter and melts at 133°–134° C.

EXAMPLE 9

2-[9-Bromo-4-(2-chlorophenyl-6H-thieno[3,2-f][1,2,4]-triazolo-[4,3-a][1,4]-diazepin-2-yl]-ethane-1-carboxylic acid morpholide First, 2-[4-(2-chlorophenyl)-6H-thieno[3,2-f][1,2,4]-triazolo[4,3-a][1,4]-diazepin-2-yl]-ethane-1-carboxylic acid morpholide (4.4 g, 0.001 mol), m.p. 188°–189° C. (cf. Example 19) is dissolved in chloroform (44 ml), then pyridine (2 ml) and bromine (0.7 ml) are added and the mixture is stirred overnight at ambient temperature. The light brown reaction solution is washed with sodium bicarbonate/water, the organic phase is dried and the solvent is evaporated. When ether is added, the title compound (3.1 g) is obtained as bright greyish-brown crystals which melt at 181°–182° C.

$^1$H-NMR (CDCl$_3$): δ=2.66 (2t, CH$_2$CO), 3.17 (2t, CH$_2$), 3.31–3.75 (8m, morpholine), 4.95 (2s, CH$_2$), 6.46 (1s, thiophene), 7.30–7.55 (4m, aryl)

EXAMPLE 10

2-[4-(2-Chlorophenyl)-9-methoxy-6H-thieno[3,2-f][1,2,4]-triazolo-[4,3-a][1,4]-diazepin-2-yl]-ethane-1-carboxylic acid morpholide The 9-bromo compound (2.6 g, 0.5 mmol) of Example 9 is stirred with a solution of caustic potash (3.7 g) in methanol (400 ml) for 1 hour at 50°–60° C. After evaporation of the methanol, the residue is mixed with ice water and extracted with methylene chloride. The organic phase is dried and the solvent is evaporated in vacuo. The residue remaining is recrystallised from ethyl acetate, to produce the title compound (1.8 g), m.p. 163°–164° C.

$^1$-H-NMR (CDCl$_3$): δ=2.62 (2t, CH$_2$), 3.11 (2t, CH$_2$), 3.32–3.77 (8m, morpholino), 4.27 (3s, CH$_3$), 4.88 (2s, CH$_2$), 6.36 (1s, thiophene), 7.36 (4s, aryl).

EXAMPLE 11

8-[4-(2-Chlorophenyl)-9-cyclopropyl-6H-thieno[3,2-f][1,2,4]-triazolo[4,3-a][1,4]diazepin-2-yl]-n-octane-1-carboxylic acid morpholide The corresponding carboxylic acid (4.63 g, 0.01 mol) is converted into the amide by means of cyclohexylcarbodiimide analogously to the process described in Example 1. A viscous oil (4.4 g) is obtained.

$^1$H-NMR (CDCl$_3$); δ=1.12–1.14 (12m, (CH$_2$)$_6$), 2.72 (3s, CH$_3$), 2.68 (2t, CH$_2$-CO), 3.15 (2t, CH$_2$), 3.31–3.78 (8m, morpholine), 4.90 (2s, CH$_2$), 6.42 (1s, thiophene), 7.25–7.60 (4m, aryl)

The starting compound for the carboxylic acid is methyl 9-formyl-nonanecarboxylate, b.p.$_{.005}$ 101°–104° C., which is obtained according to R. A. Volkmann et al., J. Org. Chem. 48, 1767 (1938).

The following compounds are also obtained using the methods described hereinbefore:

| Example No. | R$_1$ | -N(R$_2$)(R$_3$) | R$_4$ | n | Mp. °C. | Spectrum |
|---|---|---|---|---|---|---|
| 12 | CH$_3$ | CH$_3$—NH— | 2-Cl-phenyl | 2 | 166–167 | $^1$H-NMR(CDCl$_3$); δ=2,50(2t, CH$_2$—CO), 2,70 (3s, CH$_3$), 2,79(3d, CH$_3$N), 3,31(2t, CH$_2$), 4,85(2s, CH$_2$), 5,85(1q, NH), 6,45(1s, Thiophene), 7,25–7,57(4m, Aryl) |
| 13 | CH$_3$ | (CH$_3$)$_2$CH—NH— | " | 2 | Oil | $^1$H-NMR(CDCl$_3$); δ=1,11(6d(CH$_3$)-Isoprop.), 2,45(2t, CH$_2$CO), 2,68(3s, CH$_3$), 3,12(2t, CH$_2$), 4,08(1m CH-Isoprop.), 4,91(2s, CH$_2$), 5,48(1d, NHCO), 6,45(1s, Thiophene), 7,22–7,57(4m, Aryl) |
| 14 | CH$_3$ | (CH$_3$)$_2$N— | " | 2 | 157–158 | $^1$H-NMR(CDCl$_3$); δ=2,63(2t, CH$_2$—CO), 2,71 (3s, CH$_3$), 2,97(6s, N(CH$_3$)$_2$), 3,13(2t, CH$_2$), 4,14(2s, CH$_2$), 6,44(1s, Thiophene), 7,28–7,57(4m, Aryl) |
| 15 | CH$_3$ | pyrrolidin-1-yl | 2-Cl-phenyl | 2 | 167–168 | $^1$H-NMR(CDCl$_3$); δ=1,64–2,20(4m, Pyrrazole), 2,57(2t, CH$_2$—CO), 2,70(3s, CH$_3$), 3,14(2t, CH$_2$), 3,24–3,57(4m, Pyrrazole), 4,41(2s, CH$_2$), 6,42(1s, Thiophene), 7,26–7,52(4m, Aryl) |

-continued

| Example No. | R₁ | -N(R₂)(R₃) | R₄ | n | Mp. °C. | Spectrum |
|---|---|---|---|---|---|---|
| 16 | $CH_3$ | piperidin-1-yl | 2-chlorophenyl | 2 | 143–145 | ¹H-NMR(CDCl₃); δ=1,33–1,77(6m, Piperidine), 2,62(2t, CH₂—CO), 2,71(3s, CH₃), 3,13 (2t, CH₂), 3,35, 3,55(4m, Piperidine), 4,93 (2s, CH₂), 6,42(1s, Thiophene), 7,24–7,57 (4m, Aryl) |
| 17 | $CH_3$ | 4-methylpiperazin-1-yl | 2-chlorophenyl | 2 | Oil | ¹H-NMR(CDCl₃); δ=2,32(3s, NCH₃), 2,39 (4t, Piperazine), 2,65(2t, CH₂—CO), 2,73 (3s, CH₃), 3,16, 3,46(4t, Piperazine), 3,65 (2t, CH₂), 4,95(2s, CH₂), 6,45(1s, Thiophene), 7,29–7,58(4m, Aryl) |
| 18 | cyclopropyl | $N(C_2H_5)_2$ | 2-chlorophenyl | 2 | Oil | ¹H-NMR(CDCl₃); δ=0,93–1,35(10m, Cyclopropyl, C₂H₅), 1,93–2,26(1m, CH-Cyclopropyl), 2,62(2t, CH₂CO), 3,00–3,53(6m, C₂H₅ and CH₂), 4,91(2s, CH₂), 6,46(1s, Thiophene), 7,24–7,57 (4m, Aryl) |
| 19 | H | morpholin-4-yl | 2-chlorophenyl | 2 | 188–190 | ¹H-NMR(CDCl₃); δ=2,63(2t, CH₂—CO), 3,14 (2t, CH₂), 3,32–3,67(8m, Morpholine), 5,03 (2s, CH₂), 6,42(1s, Thiophene), 7,25–7,42 (4m, Aryl), 8,46(1s, Triazole) |
| 20 | $CH_3$ | $NH_2$ | 2-chlorophenyl | 1 | 202–204 | ¹H-NMR(CDCl₃); δ=2,70(3s, CH₃), 3,75 (2s, CH₂—NH₂), 4,90(2s, CH₂-7-Ring), 5,54–6,48 (2m, NH₂), 6,53(1s, Thiophene), 7,18–7,56 (4m, Aryl). |
| 21 | $CH_3$ | $N(CH_2CH_2OH)_2$ | 2-chlorophenyl | 2 | Oil | ¹H-NMR(CDCl₃); δ=2,16(2s, OH), 2,69 (3s, CH₃), 2,79(2t, CH₂CO), 3,15(2t, CH₂), 3,53–377(8m, CH₂—CH₂—OH, 4,90(2s, CH₂-7-Ring), 6,45(1s, Thiophene), 7,22–7,63(4m, Aryl). |
| 22 | $CH_3$ | morpholin-4-yl | phenyl | 2 | 180–181 | ¹H-NMR(CDCl₃); δ=2,70(2t, CH₂), 2,70(3s, CH₃), 3,22(2t, CH₂), 3,36–3,80(8m, Morpholine), 4,85(2s, CH₂), 6,73(1s, Thiophene, 7,24–7,72 (5m, Aryl) |
| 23 | $CH_3$ | $HO(CH_2)_2$—N— | 2-chlorophenyl | 2 | Oil | ¹H-NMR(CDCl₃); δ=3,50(1s, OH), 2,54(2t, CH₂CO), 2,65(3s, CH₃), 3,11(2t, CH₂), 3,38 (2m, NCH₂), 3,65(2t, OCH₂), 4,86(2s, CH₂), 6,44(1s, Thiophene), 6,88(1t, NH—CO), 7,25–7,55(4m, Aryl) |
| 24 | $CH_2Cl$ | morpholin-4-yl | 2-chlorophenyl | 2 | 163–165 | ¹H-NMR(CDCl₃); δ=2,64(2t, CH₂CO), 3,16 (2t, CH₂), 3,28–3,78(8m, Morpholine), 4,94 (4s, CH₂Cl, CH₂-7-Ring)6,41(1s, Thiophene), 7,17–7,53(4m, Aryl). |
| 25 | $CH_2Br$ | morpholin-4-yl | 2-chlorophenyl | 2 | Oil | ¹H-NMR(CDCl₃); δ=2,58(2t, CH₂CO), 3,11(2t, CH₂), 3,22–3,74(8m, Morpholine), (2s, CH₂Br), 4,98(2s, CH₂-7-Ring), (1s, Thiophene), 7,21–7,71(4m, Aryl) |

-continued

| Example No. | $R_1$ | $R_2$ / $-N$ \ $R_3$ | $R_4$ | n | Mp. °C. | Spectrum |
|---|---|---|---|---|---|---|
| 26 | CH₃—CH₂—CH₂—O (ethyl with CH₂—O) | —N(morpholine) O | 2-chlorophenyl | 2 | Oil | $^1$H-NMR(CDCl₃); δ=1,09(3t, J=7Hz, CH₃), 1,95 (2m, CH₂—CH₃), 2,63(2t, J=7Hz, CH₂CO), 3,15 (2t, J=7Hz, CH₂-thiophene), 3,31–3,74(8m, morpholine), 4,60(2t, J=6Hz, O—CH₂), 4,90 (2s, CH₂-7-ring), 6,39(1s, thiophene), 7,39 (4s, aryl) |

PHARMACOLOGICAL TESTING

The PAF-antagonistic activity of compounds of formula I is investigated in terms of the restriction of blood platelet aggregation in vitro and antagonism of the PAF-induced bronchoconstriction in anesthetized guinea pigs, lowering of blood pressure in anesthetized rats and skin weals in rats. Furthermore, these compounds are tested for possible side effects on the central nervous system. The $LD_{50}$ is also determined as a guide to acute toxicity.

1. Tests in vitro: inhibition of blood platelet aggregation

In order to determine the PAF-antagonistic effect of substances the PAF-induced aggregation of human thrombocytes in vitro is used. To obtain thrombocyte-rich plasma (TRP), blood is taken from an uncongested vein using a plastic syringe containing 3.8% sodium citrate solution. The ratio of sodium citrate solution to blood is 1:9. After careful mixing, the citrated blood is centrifuged for 20 minutes (150×g, 1200 rpm). The thrombocyte aggregation is measured using the method developed by Born and Cross (G. V. R. Born and M. J. Cross, J. Physiol. 168, 178 (1963)). PAF being added to the TRP with constant stirring to initiate aggregation.

The test substance is added 2 to 3 minutes before the aggregation is induced in a volume of 10 μl. The solvent used is either distilled water, ethanol and/or dimethylsulfoxide. Control mixtures are given corresponding volumes of these solvents. After the initial absorption has been recorded (2 to 3 minutes) aggregation is induced with PAF ($5 \times 10^{-8}$M).

To assess the effects of substances, the maximum of the first aggregation wave is used. The maximum absorption rate induced by PAF (=maximum aggregation × 100%) is tested simultaneously in a parallel mixture (=control mixture in one of the channels of the 2-channel aggregometer) with each test mixture (second channel) and used as the 100% value.

The aggregation value achieved under the influence of the test substance is given as 100%.

Each test substance is investigated at concentrations of $10^{-3}$ to $10^{-8}$M with a random test scope of n=4 for any inhibiting effect on the PAF-induced thrombocyte aggregation. Then a concentration-activity curve is drawn up using 3 concentrations and the $IC_{50}$ is determined (concentration at 50% inhibition of aggregation). 2-[4-(2-Chlorophenyl)-9-methyl-6H-thieno-[3,2-f][1,2,4]triazolo[4,3-a][1,4]diazepin-2-yl]-ethane-1-carboxylic acid diethylamide and 2-[4-(2-chlorophenyl)-9-methyl-6H-thieno[3,2-f][1,2,4]triazolo[4,3-a][1,4]diazepino-2-yl]-ethane-1-carboxylic acid morpholide, having $IC_{50}$ values of 0.7 and 0.17, respectively, are particularly potent compounds. The results are set forth in Table B below.

TABLE B

| EXAMPLE NO. | PAF-Antag. $IC_{50}$ [μMol] |
|---|---|
| 1 | 0.17 |
| 2 | 0.33 |
| 3 | 0.71 |
| 4 | 8.3 |
| 5 | 0.72 |
| 6 | 1.3 |
| 7 | 0.85 |
| 8 | 0.87 |
| 9 | 0.47 |
| 10 | 0.2 |
| 12 | 0.35 |
| 13 | 1.54 |
| 14 | 2.2 |
| 15 | 0.38 |
| 16 | 1.33 |
| 17 | 0.9 |
| 18 | 0.8 |
| 19 | 8.2 |
| 20 | 5.3 |
| 21 | 2.9 |
| 22 | 0.54 |
| 23 | 0.75 |
| 24 | 1.4 |
| 26 | 8.1 |
| Etizolam | 0.5 |
| Brotizolam | 0.5 |
| Triazolam | 1.4 |

2. Test in vivo 2.1. Antagonizing of the PAF-induced bronchoconstriction in anesthetized quinea pigs Spontaneously breathing male guinea pigs weighing 300 to 450 g are treated orally 1 hour before intravenous infusion of PAF (30 ng/(kg×min)) with the test substance or a control vehicle. The test animals are then anesthetized by intraperitoneal route with urethane (2 mg/kg), whereupon the jugular vein, carotid artery and trachea are cannulated. PAF infusion induces a powerful and long-lasting bronchoconstriction in the control animals which is measured by means of the volume of respiration, compliance and resistance, and also a lowering of blood pressure. After about 7 to 10 minutes death occurs. Using the PAF antagonists described, these effects on breathing and blood pressure and the onset of death are prevented. The doses range from about 0.5 to about 5 mg/kg p.o. and from about 0.5 to about 1.0 mg/kg i.v.

2.2. Antagonizing of PAF-induced lowering of blood pressure in anesthetized rats Normotonic male Wistar rats weighing 200 to 250 g are anesthetized by intraperitoneal route with urethane (2 mg/kg). The carotid artery and jugular vein are cannulated. In the control animals, intravenous PAF infusion (30 ng/(kg×min)) induces a powerful and long-lasting lowering of blood pressure. This is reversed by intravenous injections (cumulative administration) of the compounds described in accordance with the invention in a dosage range of from about 0.01 to about 0.5 mg/kg. Oral or intravenous administration of the compound before the start of the PAF infusion can also prevent the hypotensive activity of the above-mentioned PAF infusion, depending on the dosage.

2.3. Antagonizing of PAF-induced skin weals in rats (modified according to P. P. Koelzer and K. H. Wehr, Arzneim.-Forsch. 8, 181 (1958))

Intracutaneous injection of PAF induces skin weals which indicate a PAF-induced increase in the permeability of the blood vessels.

Male Wistar rats with a body weight of 250±20 g are shaved over their abdominal walls. Then a 1% trypane blue solution (1 ml/kg) is injected into the animals through a vein in the tail. Symmetrically with respect to the central line (linear alba) at three points about 1.5 cm apart, intracutaneous injections of physiological saline solution or PAF solution (12.5 to 25.0 ng/site in 0.1 ml) are administered. Whereas there is no reaction at the point of injection of the saline solution, PAF induces a skin reaction (weals) which is made visible by blue coloration of varying intensity, depending on the dosage of PAF. By simultaneously administering the compounds described by intracutaneous route in doses of from about 0.5 to about 5 μg/site (in 0.1 ml) or by intravenous pre-treatment in doses of 0.2 to 3 mg/kg this PAF-induced skin reaction is prevented.

3. Effects on the central nervous system

It is generally known that substances of this type of structure cause central nervous effects which are undesirable for a compound with a PAF-antagonistic effect. Therefore, the compounds described are tested for their hypnotic and anticonvulsive activities and for their effects on locomotion. Possible hypnotic effects are tested on guinea pigs weighing 400 to 450 g. Dosages of up to 200 mg/kg p.o. of these substances do not produce any hypnotic or sedative effects in these animals.

Anticonvulsive activities are tested using the pentetrazole antagonism in mice (body weight 20 to 25 g) (M. I. Gluckmann, Current Therapeutic Research 7:721, 1965). Doses of up to 100 mg/kg p.o. of these compounds (1 hour before pentetrazole) showed no effect on the mortality caused by pentetrazole (125 mg/kg i.p., LD 100) in this test. The effects on night motility (locomotion) in mice (body weight 20 to 25 g) can be investigated in a light beam cage. The number of times the light beam is broken is measured. Doses of up to 300 mg/kg p.o. of the compounds mentioned above showed no activity.

4. Acute toxicity in mice

The average lethal dose ($LD_{50}$) after oral administration is between 3 and 4 g/kg for the compounds on which tests are performed. The $LD_{50}$ values after intravenous administration ranged from 400 to 700 mg/kg.

The compounds of formula I can be administered to warm-blooded animals topically, orally, parenterally or by inhalation. The compounds are presented as active substances in conventional preparations, e.g. in compositions comprising an inert pharmaceutical vehicle and an effective dose of the active substance, such as plain or coated tablets, capsules, lozenges, powders, solutions, suspensions, aerosols for inhalation, ointments, emulsions, syrups, suppositories, etc. An effective dose of the compounds according to the invention is between 1 and 50, preferably between 3 and 20 mg/dose for oral use, between 0.01 and 50, preferably between 0.1 and 10 mg/dose for intravenous or intramuscular use. For inhalation, solutions are used containing 0.01 to 1.0, preferably 0.1 to 0.5% of active substance.

Examples of some pharmaceutical compositions containing compounds of formula I as active ingredient will now be given. Unless otherwise expressly stated, the parts are parts by weight.

1. Tablets

The tablets contain the following ingredients:

| | |
|---|---|
| Active substance of formula I | 0.020 parts |
| Stearic acid | 0.010 parts |
| Dextrose | 1.890 parts |
| total | 1.920 parts |

Preparation

The substances are mixed together in known manner and the mixture is compressed to form tablets (1.92 g) containing active substance (20 mg).

2. Ointment

The ointment contains the following ingredients:

| | |
|---|---|
| 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 50 mg |
| Neribas ointment (commercial product Scherax) ad | 10 g |

Preparation:

The active substance is triturated with ointment base (0.5 g) and the remaining base is added in batches (1.0 g) gradually and intimately mixed to form an ointment. An ointment (0.5%) is obtained. The distribution of the active substance in the base is monitored optically under a microscope.

3. Cream

Composition

| | |
|---|---|
| 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 50 mg |
| Neribas ointment (commercial product Scherax) ad | 10 g |

Preparation

The active substance is triturated with cream base (0.5 g) and the remaining base is gradually incorporated in amounts with a pestle (1.0 g). A cream (0.5%) is obtained. The distribution of the active substance in the base is monitored optically under a microscope.

4. Ampoule solution

Composition

| | |
|---|---|
| (a) 2-[4-(2-Chlorophenyl)-9-methyl-6H-thieno-[3,2-f][1,2,4]triazolo[4,3-a][1,4]diazepin- | 1.0 mg |

| | |
|---|---|
| 2-yl]-ethane-1-carboxylic acid morpholide | |
| Sodium chloride | 45.0 mg |
| Water for injection ad | 5.0 ml |
| (b) 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 5.0 mg |
| Sodium chloride | 45.0 mg |
| Water for injection ad | 5.0 ml |
| (c) 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 1.0 mg |
| Sodium chloride | 9.0 mg |
| Water for injection ad | 1.0 ml |

Preparation

The active substance is dissolved in water at its own pH and sodium chloride is added as an isotonic substance. The resulting solution is filtered to remove pyrogens and the filtrate is transferred under aseptic conditions into ampoules which are then sterilized and sealed by fusion. The ampoules contain 1 mg, 5 mg and 1 mg of active substance.

5. Suppositories

Each suppository contains

| | |
|---|---|
| 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 1.0 parts |
| Cocoa butter (m.p. 36–37° C.) | 1200.0 parts |
| Carnauba wax | 5.0 parts |

Preparation

The cocoa butter and carnauba wax are melted together. At 45° C. the active substance is added and the mixture is stirred until a complete dispersion is formed. The mixture is poured into moulds of suitable sizes and the suppositories are appropriately packaged.

6. Solutions for inhalation

Composition

| | |
|---|---|
| (a) 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 500 mg |
| Na-EDTA | 50 mg |
| Benzalkonium chloride | 25 mg |
| Sodium chloride | 880 mg |
| Distilled water ad | 100 ml |

Preparation

96% of the quantity of water is put in first, then the Na-EDTA, benzalkonium chloride, sodium chloride and active substance are dissolved successively therein until a clear solution is formed and the remainder of the water is added. The solution is poured into drop vials (20 ml). One dose (20 drops, 1 ml) contains 5 mg of active substance.

| | |
|---|---|
| (b) 2-[4-(2-Chlorophenyl)-9-methyl-6H-thieno-[3,2-f][1,2,4]triazolo[4,3-a][1,4]diazepin-2-yl]-ethane-1-carboxylic acid morpholide | 500 mg |
| Sodium chloride | 820 mg |
| Distilled water ad | 100 ml |

Preparation

96% of the quantity of water is put in first, then the active substance and sodium chloride are successively dissolved therein, the remaining water is added and the solution is transferred into single dose containers (4 ml). The solution contains 20 mg of active substance.

What is claimed is:

1. Thieno-triazolo-1,4-diazepino-2-carboxylic acid amides having the formula wherein
$R_1$ represents hydrogen, a $C_1$–$C_4$ straight-chained or branched alkyl group which can optionally be substituted by halogen or hydroxy, cyclopropyl, $C_1$–$C_3$ alkoxy, or halogen:
$R_2$ and $R_3$, each independently, represent hydrogen, a $C_1$–$C_4$ straight-chained or branched alkyl or hydroxyalkyl group or both groups $R_2$ and $R_3$ together with the nitrogen atom represent a 5-, 6- or 7-membered ring which optionally contains a nitrogen, oxygen or sulphur atom as a further heteroatom, the second nitrogen atom optionally being substituted by a $C_1$–$C_4$ alkyl group:
$R_4$ represents alpha-pyridyl or a phenyl, in which the phenyl ring can be substituted in the 2-position or in the 2- and 6-positions by methyl, halogen, nitro or trifluoromethyl; and
n represents one of the numbers 0, 1, 2, 3, 4, 5, 6, 7 or 8.

2. Thieno-triazolo-1,4-diazepino-2-carboxylic acid amides of claim 1, wherein
$R_4$ represents phenyl, 2-chlorophenyl or 2-bromophenyl and
n represents the number 1, 2 or 3.

3. Thieno-triazolo-1,4-diazepino-2-carboxylic acid amides of claim 1, wherein
$R_1$ represents hydrogen, a $C_1$–$C_4$ straight-chained or branched alkyl group, cyclopropyl, methoxy, chlorine or bromine;
$R_2$ and $R_3$ each independently represent hydrogen, methyl, ethyl, hydroxyethyl or together with a nitrogen atom they represent morpholine;
$R_4$ represents 2-chlorophenyl or 2-bromophenyl; and
n represents the number 2.

4. 2-[4-(2-Chlorophenyl)-9-methyl-6H-thieno[3,2-f][1,2,4]-triazolo[4,3-a][1,4]diazepin-2-yl]-ethane-1-carboxylic acid morpholide.

5. 2-[4-(2-Chlorophenyl)-9-methyl-6H-thieno[3,2-f][1,2,4]-triazolo[4,3-a][1,4]diazepin-2-yl]-ethane-1-carboxylic acid diethylamide.

6. A platelet activating factor antagonistic pharmaceutical composition comprising a platelet-activating factor antagonistic amount of a compound of claim 1 and a nontoxic, pharmaceutically acceptable carrier.

7. A method of treating an individual afflicted with a pathological condition in which platelet activating factor is implicated which comprises administering to the individual so-afflicted a therapeutically effective dose of a compound of claim 1.

* * * * *